(12) United States Patent
Honda et al.

(10) Patent No.: US 7,252,648 B2
(45) Date of Patent: Aug. 7, 2007

(54) ULTRASOUND PUNCTURE SYSTEM

(75) Inventors: Yoshitaka Honda, Hachioji (JP); Kenji Noda, Machida (JP); Manabu Ishikawa, Akiruno (JP); Shuichi Kimura, Hachioji (JP); Kenichi Kimura, Hachioji (JP); Daisuke Sano, Hachioji (JP)

(73) Assignee: Olympus Corporation, Tokyo (JP)

( * ) Notice: Subject to any disclaimer, the term of this patent is extended or adjusted under 35 U.S.C. 154(b) by 159 days.

(21) Appl. No.: 10/791,454

(22) Filed: Mar. 2, 2004

(65) Prior Publication Data

US 2004/0176717 A1 Sep. 9, 2004

(30) Foreign Application Priority Data

Mar. 7, 2003 (JP) .............................. 2003-062050

(51) Int. Cl.
*A61B 17/20* (2006.01)
(52) U.S. Cl. ................................................. 604/22
(58) Field of Classification Search .................. 604/22; 606/1; 600/439, 547–548
See application file for complete search history.

(56) References Cited

U.S. PATENT DOCUMENTS 5,076,276 A * 12/1991 Sakurai et al. ................. 601/2
5,520,633 A * 5/1996 Costin ......................... 604/22
5,728,130 A * 3/1998 Ishikawa et al. ............ 606/185
6,383,183 B1 * 5/2002 Sekino et al. ................ 606/34

FOREIGN PATENT DOCUMENTS

| JP | 03-146048 | 6/1991 |
|---|---|---|
| JP | 7-51281 | 2/1995 |
| JP | 2001-104322 | 4/2001 |

* cited by examiner

*Primary Examiner*—Brian L. Casler
*Assistant Examiner*—Francis J. Jaworski
(74) *Attorney, Agent, or Firm*—Scully, Scott, Murphy & Presser, P.C.

(57) ABSTRACT

The ultrasound puncture system in accordance with the present invention comprises a handpiece which accommodates an ultrasound vibrator, a puncturing probe for transmitting ultrasound waves to a biological wall which is to be punctured, an outer cover tube covering the probe and attached to the handpiece, and an ultrasound power source unit for driving the ultrasound vibrator, wherein the ultrasound power source unit comprises a termination unit for terminating the energy supply to the ultrasound vibrator, an impedance detector for detecting the puncture state of the probe, and a fluid supply unit for supplying a fluid to the distal end opening of the outer cover tube and probe, wherein the penetration of the probe through the biological wall is detected with the detection unit and the supply of energy to the ultrasound vibrator is terminated based on the detection output.

8 Claims, 13 Drawing Sheets

ULTRASOUND PUNCTURE SYSTEM

CROSS-REFERENCE TO RELATED APPLICATION

This application claims benefits of Japanese Application No. 2003-62050 filed in Japan on March 7, the contents of which are incorporated by this reference.

BACKGROUND OF THE INVENTION

1. Field of the Invention

The present invention relates an ultrasound puncture system for conducting the prescribed treatment by puncturing the abdominal wall or the like by employing ultrasound vibrations.

2. Description of the Related Art

Examples of ultrasound puncture systems for conducting the prescribed treatment by puncturing the abdominal wall or the like by employing ultrasound vibrations are described in Japanese Patent Applications Laid-open No. 7-51281 and 2001-104322.

Japanese Patent Application Laid-open No. 7-51281 discloses an ultrasound trocar for conducting puncturing so as to form a puncture hole in a tissue with ultrasound vibrations by using a probe with a rounded distal end. In this ultrasound trocar, whether or not the puncture hole has been formed in the tissue is decided by detecting the phase difference between the impedance of the probe, the output voltage, and the output current. Furthermore, with the aforesaid ultrasound trocar, the tissue damage by the puncture hole can be prevented by fixing the ultrasound vibration level of the vibrating distal end portion or by stopping the operation in an inactive idling state in the prescribed cases.

On the other hand, Japanese Patent Applications Laid-open No. 2001-104322 discloses an ultrasound trocar in which a through hole is formed in the distal end portion of the ultrasound probe and a rod-shaped member elastically held by an elastic impelling means is inserted into the through hole. In this ultrasound trocar, piercing of the tissue with the distal end of the probe is detected by the movement of the rod-shaped member when the distal end of the probe punctures the tissue.

SUMMARY OF THE INVENTION

Briefly, the ultrasound puncture system in accordance with the present invention comprises a handpiece which accommodates an ultrasound vibrator, a puncture probe for transmitting ultrasound waves to a biological wall which is to be punctured, an outer cover tube covering the probe and attached to the handpiece, and an ultrasound power source unit for driving the ultrasound vibrator, wherein the ultrasound power source unit comprises a termination unit for terminating the energy supply to the ultrasound vibrator, an impedance detector for detecting the puncture state of the probe, and a fluid supply unit for supplying a fluid to the distal end opening of the outer cover tube and probe, wherein the penetration of the probe through the biological wall is detected with the detecting unit and the supply of energy to the ultrasound vibrator is terminated based on the detected output.

Additional features and advantages of the invention will be set forth in the description which follows, and in part will be obvious from the description, or may be learned by practice of the invention. The features and advantages of the invention may be realized and obtained by means of the instrumentalities and combinations particularly pointed out hereinafter.

DESCRIPTION OF THE PREFERRED EMBODIMENTS

Embodiments of the present invention will be described hereinbelow with reference to the drawings.

Figure 1:
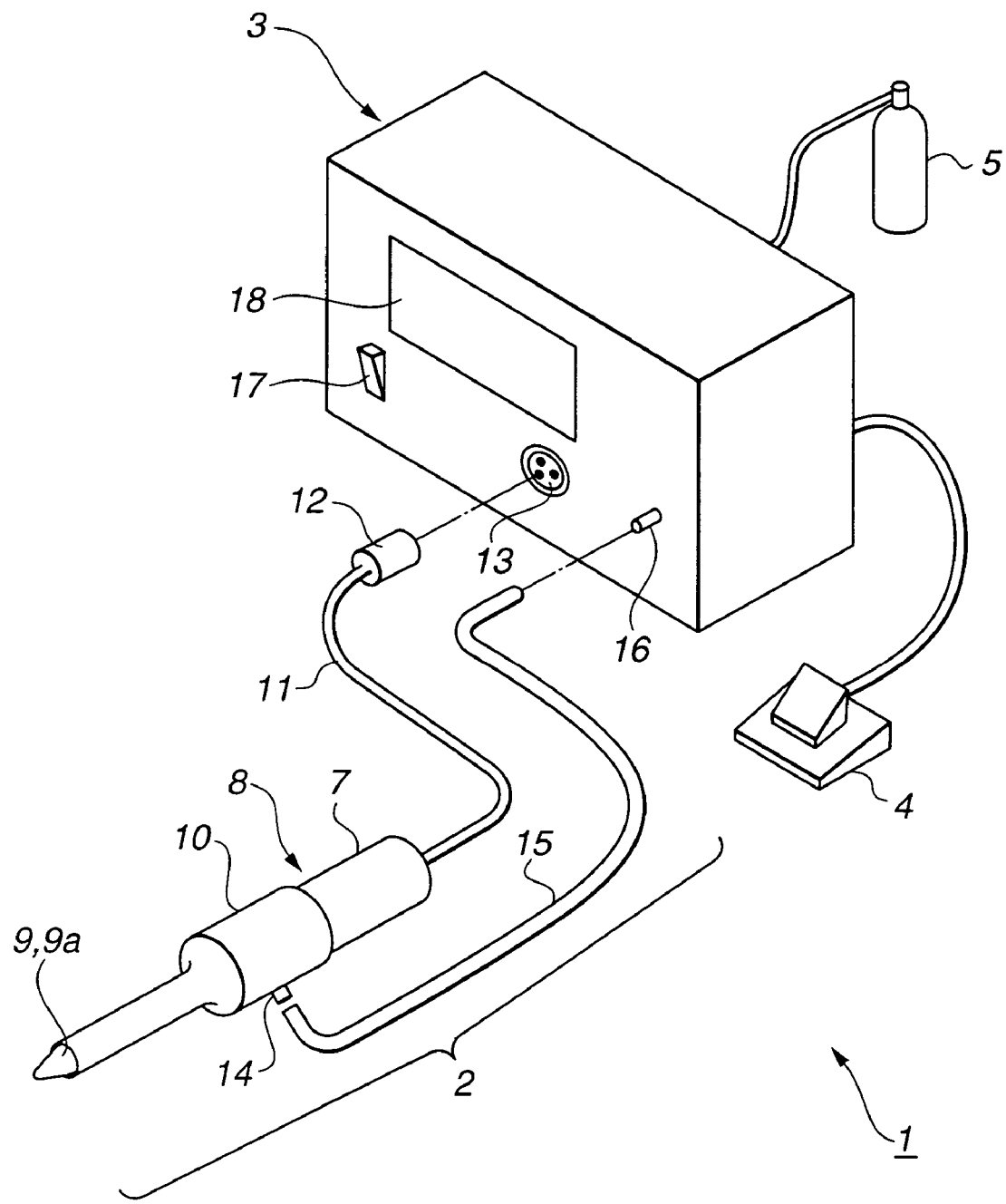
FIG. 1 is a perspective view illustrating the overall configuration of the ultrasound puncture system of a first embodiment of the present invention.
Figure 2:
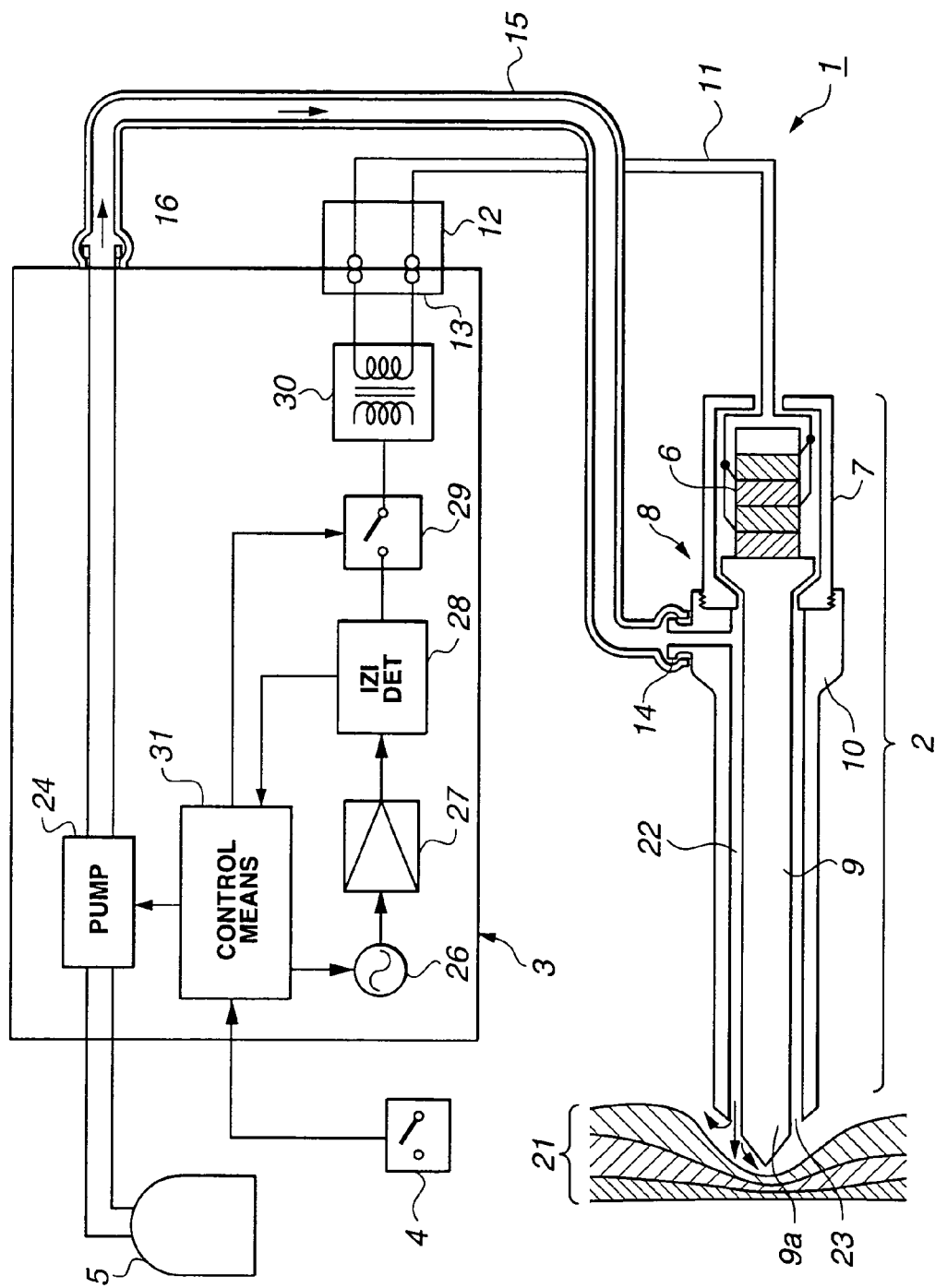
FIG. 2 is a block diagram illustrating the internal configuration of the ultrasound puncture system of the first embodiment.
Figure 3:
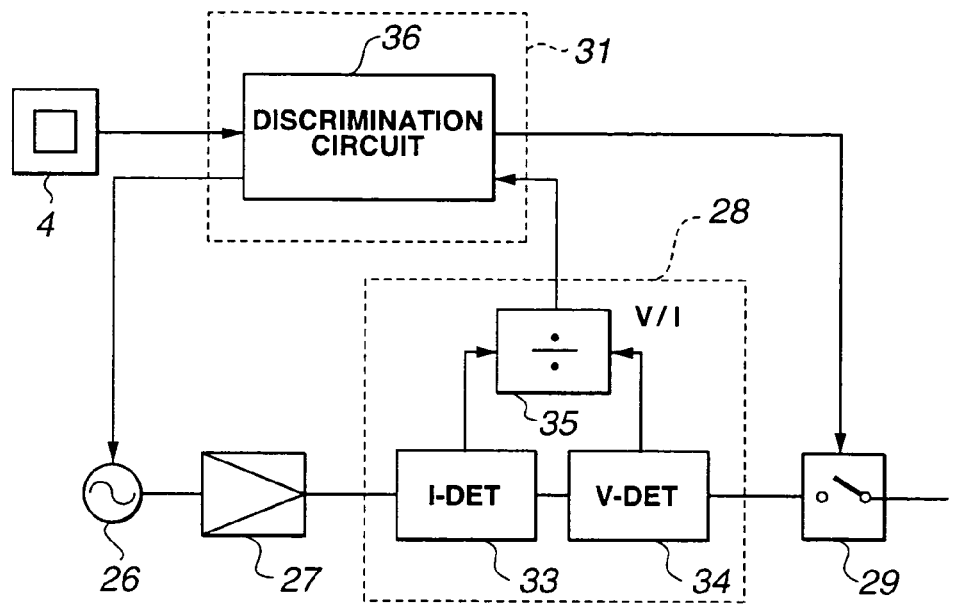
FIG. 3 is a block diagram illustrating the configuration of the drive impedance detection circuit in the ultrasound puncture system of the first embodiment.
Figure 4:
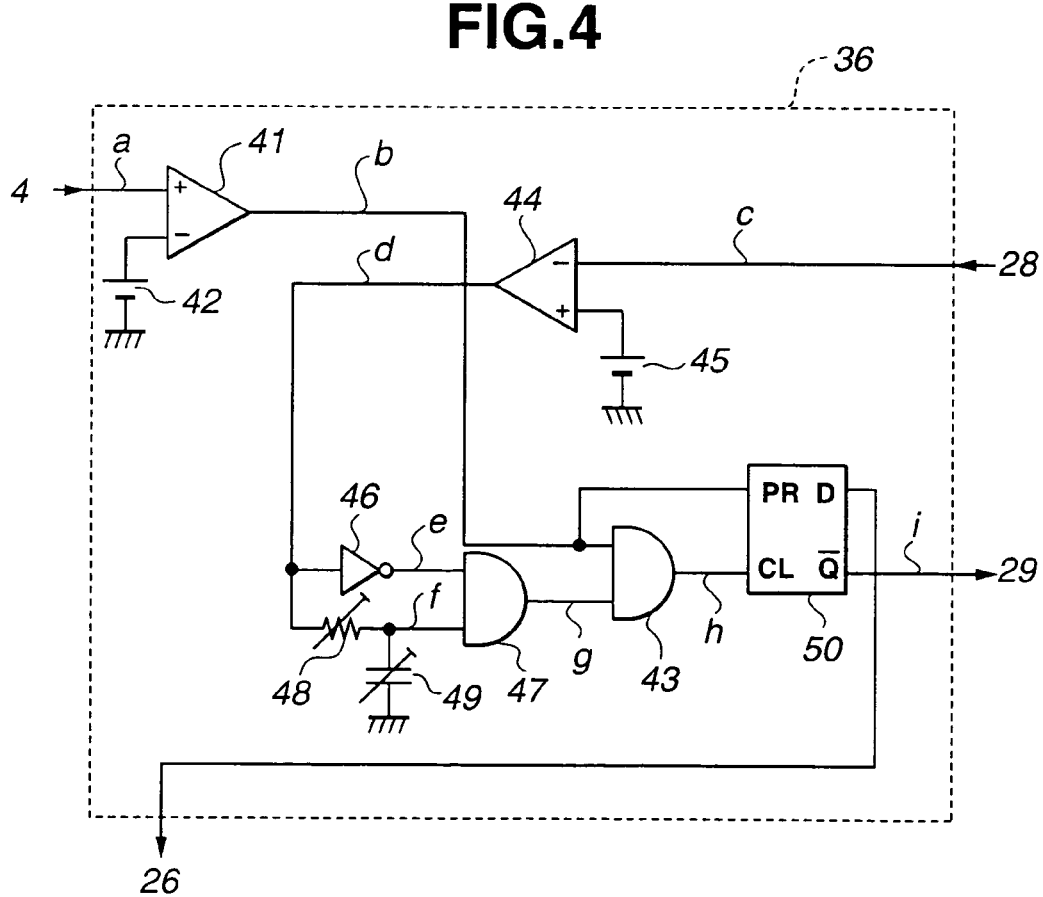
FIG. 4 is a circuit diagram illustrating the internal configuration of the discrimination circuit in the ultrasound puncture system of the first embodiment.
Figure 5:
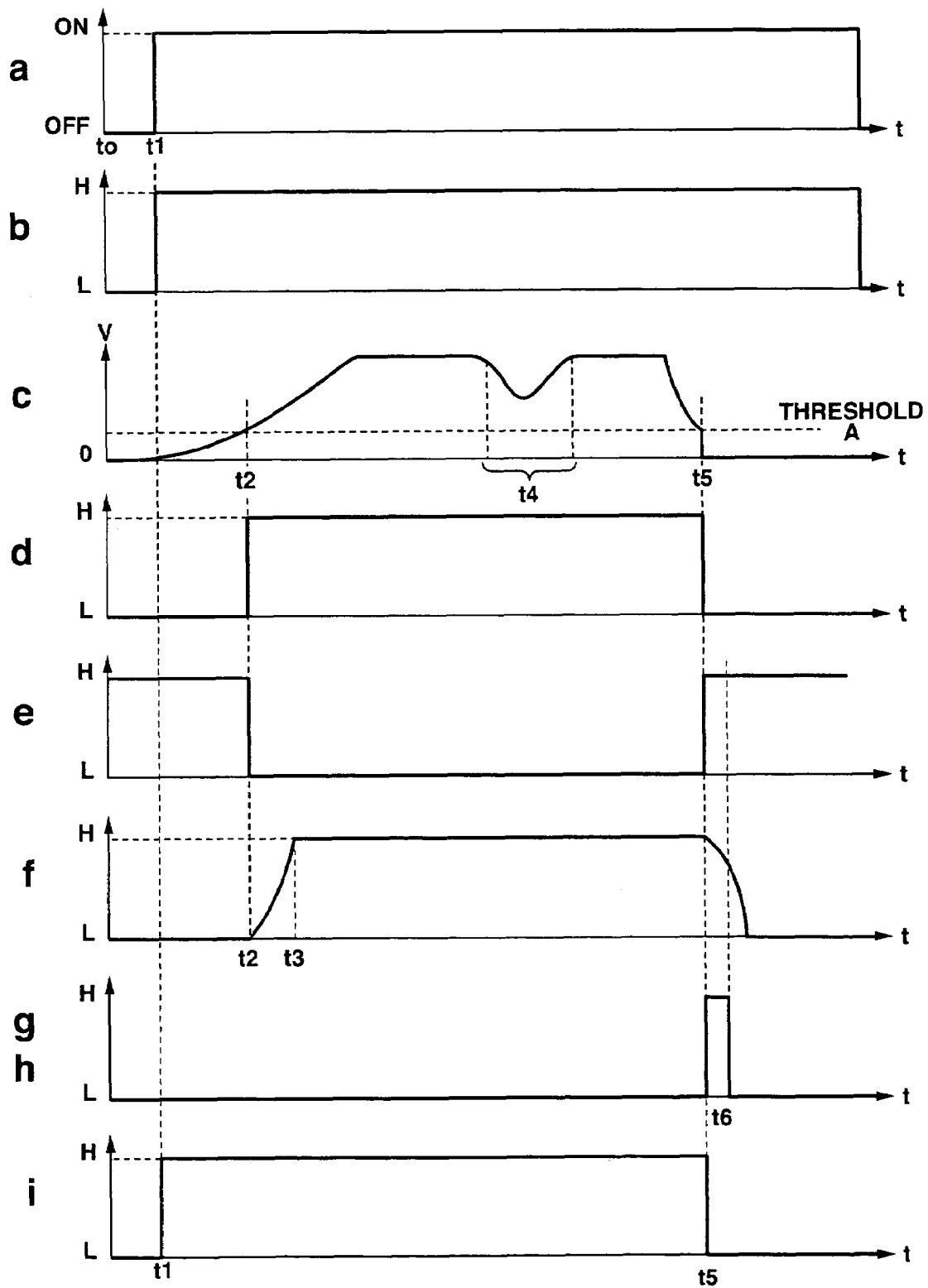
FIG. 5 is a timing chart illustrating the operation of various components of the discrimination circuit in the ultrasound puncture system of the first embodiment.

FIG. 1 illustrates the overall configuration of the ultrasound puncture system of a first embodiment, FIG. 2 shows the internal configuration of the structure shown in FIG. 1, FIG. 3 shows the configuration of a drive impedance detection circuit, FIG. 4 shows the internal configuration of a discrimination circuit, and FIG. 5 shows the operation of the various components of the discrimination circuit based on waveform thereof.

As shown in FIG. 1, the ultrasound puncture system 1 in accordance with the present invention comprises an ultrasound puncture treatment tool 2 for puncturing by ultrasound, a power source unit 3 for supplying high-frequency electric energy for driving the ultrasound puncture treatment tool 2, an output switch 4 connected to the power source unit 3 and formed, for example, of a foot switch for conducting ON/OFF of the electric energy supplied from the power source unit 3 to the ultrasound puncture treatment tool 2, and a fluid tank 5 connected to the power source unit 3 and containing a fluid which is to be supplied to the ultrasound puncture treatment tool 2.

The ultrasound puncture treatment tool 2 comprises a handpiece 8 which is provided on the proximal end side of the treatment tool and a vibrator accommodating unit 7 accommodating an ultrasound vibrator 6, this unit being held by an operator, an ultrasound probe 9 connected by the base end thereof to the handpiece 8 for conducting the puncture treatment by transmitting ultrasound waves to the distal end portion 9a that is tapered to have a conical shape, and an outer cover tube 10 which is detachably mounted on the handpiece 8 and covers the ultrasound probe 9.

In the ultrasound puncture treatment tool 2, an electric cable 11 is extended from the rear end of the handpiece 8, and an electric plug 12 provided at the rear end of the electric cable 11 is detachably connected to an output connector 13 of the power source unit 3, such a connection making it possible to supply high-frequency electric energy from the power source unit 3 to the ultrasound vibrator 6.

Furthermore, one end of a tube 15 is connected to a socket 14 on the outer peripheral portion of the rear end portion in the outer cover tube 10 attached to the handpiece 8, and the other end of the tube 15 is detachably connected to the fluid supply connector 16 of the power source unit 3, such a connection making it possible to supply a fluid from the fluid tank 5 to the distal end side of the ultrasound probe 9 via the inner side of the outer cover tube 10.

The power source unit 3, for example, comprises on the front surface thereof the above-mentioned output connector 13 and fluid supply connector 16 and also a power source switch 17 for switching the power source ON/OFF and a front panel 18 for displaying or setting the output state.

FIG. 2 shows the internal configuration of the system shown in FIG. 1 in a state in which treatment with the ultrasound puncture treatment tool 2 is conducted, for example, with respect to a skin tissue 21 as a puncturing object.

The ultrasound vibrator 6 having a function of electroacoustic conversion is disposed inside the vibrator accommodating unit 7 forming the handpiece 2, this ultrasound vibrator being formed, for example, of a plurality of disk-shaped piezoelectric elements tightened together with bolts, with electrodes being mounted on both surfaces thereof. The electric plug 12 provided at the end portion of the electric cable 11 connected to the electrodes is connected to the output connector 13 of the power source unit 3. As a result, ultrasound vibrations can be induced by applying high-frequency electric energy to the ultrasound vibrator 6.

A base end portion, for example, expanded to assume a taper-like shape, of the rod-like ultrasound probe 9 is tightly joined to the front end surface of the ultrasonic vibrator 6, and the ultrasound vibrations created by the ultrasonic vibrator 6 are transferred to the distal end portion 9a of the ultrasound probe 9.

The base end portion of the cover tube 10 is detachably attached, for example, by screwing, to the front end of the vibrator accommodating unit 7, the ultrasound probe 9 is inserted into the empty space inside the outer cover tube 10 so that a clearance 22 is formed therebetween, and the pointed distal end portion 9a of the ultrasound probe 9 slightly protrudes from the opening 23 at the distal end of the outer cover tube 10, thereby providing a shape that can be easily used for puncturing. A socket 14 is provided in the base end portion of the outer cover tube 10 and connected to a fluid supply connector 16 of the power source unit 3 via a tube 15.

A pump 24 is contained in the power source unit 3, one end of the pump being connected to a fluid tank 5 and the other end being connected to a fluid supply connector 16. The fluid present in the fluid tank 5 is supplied by the pump 24 to the socket 14 of the outer cover tube 10 via the tube 15 connected to the fluid supply connector 16. From the socket 14, the fluid can be further supplied into the opening 23 at the distal end side via the clearance 22 of the outer cover tube 10 formed by the ultrasound probe 9 inserted therein.

Further, an oscillator 26 which oscillates at a frequency necessary for ultrasonic excitation of the ultrasound vibrator 6 is provided inside the power source unit 3, and the oscillation signal of the oscillator 26 is power amplified with an amplifier 27 and becomes a vibrator drive signal as electric energy for driving the vibrator.

The vibrator drive signal passes through a drive impedance detection circuit 28 that detects the current component and voltage component of the signal and detects the drive impedance of the ultrasound puncture treatment tool 2, passes through an interruption switch 29 provided on the power feed line of the vibrator drive signal, then passes through the insulation transformer 30 for transferring the vibrator drive signal to the secondary side, while maintaining electric insulation, and is applied to the ultrasound vibrator 6 from the output connector 13 via a signal cable 11.

Furthermore, control means 31 for controlling the operation of the entire power source unit 3 is provided inside the power source unit 3. The control means 31 is connected to the output switch 4, pump 24, oscillator 26, drive impedance detection circuit 28, and interruption switch 29.

The control means 31 conducts, according to the operation of the output switch 4, the control of oscillation and termination of the oscillator 26, the control of operation of pump 24, the control of interruption switch 29, the control of electric energy supply termination to the ultrasound vibrator 6 by OFF (from ON) of the interruption switch 29 according to the results of drive impedance detection obtained with the drive impedance detection circuit 28, and the display control in the front panel 18. The control means 31 also conducts the control for setting the pump 24 to the operation state when the puncture treatment is being conducted.

In this embodiment, when puncture of a puncture object, for example, the skin tissue 21, is conducted with the distal end portion 9a of the ultrasound probe 9, as shown in FIG. 2, by using the ultrasound puncture treatment tool 2, the configuration makes it possible to supply a fluid through the clearance 22 inside the outer cover tube 10 that covers the outer peripheral surface of the treatment zone, thereby preventing the foreign matter such as body fluids or tissue from penetrating to the periphery of the distal end portion 9a.

Thus preventing the foreign matter such as body fluids or tissue from penetrating into the opening 23 at the distal end of the outer cover tube 10 increases the accuracy of impedance detection conducted to detect the puncture state.

The configuration of the drive impedance detection circuit 28 will be explained hereinbelow with reference to FIG. 3.

The output signal from the amplifier 27 is inputted into the electric current detection circuit 33 constituting the drive impedance detection circuit 28, and the phase and amplitude of the electric current component in the vibrator drive signal is detected with the electric current detection circuit 33.

Further, the phase and amplitude of the voltage component of the vibrator drive signal are detected by a voltage detection circuit 34, the output signals of the two detection circuits 33, 34 are inputted into a divider 35, where the detected voltage is divided by the detected current and a drive impedance is detected. The drive impedance detected by the divider 35 is inputted into a discrimination circuit 36 of control means 31. Further, the vibrator drive signal that passed through the voltage detection circuit 34 is transferred to the interruption switch 29.

FIG. 4 shows the configuration of the discrimination circuit 36 (in control means 31) that inputs the drive impedance detected by the drive impedance detection circuit 28 and operation signals from the output switch 4.

The operation signal (a) from the operation switch 4 is supplied to one input terminal of a comparator 41. The output switch 4 is set so that in the OFF state, the signal is pulled down to a GND level, but switching ON results in generating the prescribed voltage, e.g., power source terminal. The comparator 41 compares the signal with a reference voltage 42 (set lower than aforesaid prescribed voltage) applied to the other input terminal and outputs a discrimination signal (b) for discriminating the ON/OFF operation of the output switch 4.

The discrimination signal (b) from the comparator 41 is applied to one input terminal of an AND gate 43 and a preset terminal PR of a D-type flip-flop 50. Only when the discrimination signal (b) is the H logic, the flip-flop 50 is set to the enable operation state.

Further, the impedance signal (c) inputted from the divider 35 of the impedance detection circuit 28 is applied to one input terminal of the comparator 44 and a discrimination signal (d) which is a comparison result (discrimination result) obtained by comparing the applied signal with the reference impedance 45 (in FIG. 4, it is shown by a voltage source, for the sake of simplicity) is applied to the other input terminal. The reference impedance is set to a threshold A (see FIG. 5) indicating the case in which the distal end portion 9a of the ultrasound probe 9 has penetrated through the skin tissue 21.

When the detected impedance value is not higher than the threshold A, a discrimination signal (d) indicating that the skin tissue 21 has been penetrated is outputted, and energy supply to the ultrasound vibrator 6 is terminated, as explained with reference to FIG. 5.

The discrimination signal (d) becomes the inverted signal (e) after passing through an inversion gate 46 that inverts the input signals and is inputted into the AND circuit 47. Furthermore, the discrimination signal (d) also becomes a signal (f) that passed (or was integrated) through a low-pass filter (LPF) that delays the rise and fall of the signal waveform with a variable resistor 48 and a variable capacitor 49, and is applied to the other input terminal of the AND gate 47.

The AND gate 47 generates a signal (g) which represents a logic sum of the inverted signal (e) and integrated signal (f), and the signal (g) is applied to the other input terminal of the AND gate 43. The AND gate 43 generates a signal (h) which represents a logic sum of the discrimination signal (b) and signal (g), and this signal (h) is applied to a clock terminal CL of the D-type flip-flop 50, and the signal fetched at the input terminal D at the rising edge is outputted.

In the D-type flip-flop 50, the input terminal D is connected to the inverted output terminal, and the output signal (i) is outputted from the inverted output terminal to the interruption switch 29 and oscillator 26.

The operation described below relates to the case in which a puncture hole for introducing a rigid endoscope or a treatment tool is provided by setting, as shown in FIG. 2, the ultrasound puncture treatment tool 2 of the present embodiment having the above-described configuration against a biological membrane, more specifically, the skin tissue 21 of the stomach.

In this case, if the output switch 4 is turned ON, the control means 31 sets the oscillator 26 into an oscillation mode and the interruption switch 29 into a closed state (ON), and drive energy for driving the ultrasound vibrator 6 is supplied to the ultrasound vibrator 6.

As a result, the drive impedance detection circuit 28 detects the respective impedance and sends it to the discrimination circuit 36 shown in FIG. 5. Based on the inputted impedance, the discrimination circuit 36 judges the puncture state when the distal end portion 9a of the ultrasound probe 9 punctures the skin tissue 21. If the detected impedance that is detected as described hereinbelow is not higher that the threshold A, the interruption switch 29 is turned OFF and the drive energy supplied to the ultrasound vibrator 6 is terminated.

Signal waveforms in all the components during the operation with the drive impedance detection circuit 28 shown in FIG. 4 are shown in FIG. 5.

The initial values of all the signals at the instant of time t0 and the initial state are as follows. The signal (a) is OFF, the signal (b) is the L logic, the signal (c) is 0 V, the signal (d) is the L logic, the signal (e) is the H logic, the signal (f) is the L logic, the signal (g) is the L logic, the signal (h) is the L logic, and the signal (i) is the L logic.

Further, if the output switch 4 is pushed at the timing of the instant of time t1, the signal (a) changes to ON. As a result, the output signal (b) of the comparator 41 changes to the H logic. Because the signal (b) changed to the H logic, the D-type flip-flop 50 is reset. Therefore, the signal (i) becomes the H logic.

The oscillator 26 to which the signal (i) is connected becomes enabled or the interruption means 29 becomes closed (conductive state).

If the drive impedance rises, and exceeds the set value of the reference impedance 45, that is, the threshold A at the timing of the instant of time t2, the output signal (d) of the comparator 44 changes to the H logic.

As a result, the signal (e) that passed through the inverted gate 46 becomes the L logic. Furthermore, because the signal (d) passes through the LPF composed of the variable resistor 48 and variable capacitor 49, the potential gradually rises till t3.

In this state, even if the decrease in the drive impedance is generated following the decrease in the puncture force in the interval t4, because the threshold A has been set to a sufficiently low value, the output signal (d) of the comparator 44 does not change to the L logic.

Then, at the instant of time t5, a decision is made by comparison with the threshold A that the distal end portion 9a of the ultrasound probe 9 of the ultrasound puncture treatment tool 2 has penetrated through the skin tissue 21 and the drive impedance has sufficiently decreased.

The signal (d) representing the decision result changes to the L logic

Accordingly, the signal (e) that passed through the inverted gate 46 changes to the H logic.

On the other hand, the level of the signal (f) that passed through the LPF composed of the variable resistor 48 and the variable capacitor 49 gradually decreases and becomes equal to or less than the threshold A of the L and H levels in the AND gate 47.

Because the signal (g) becomes the H logic only when both the signal (e) and the signal (f) are the H logic, the signal (g) becomes the H logic only within the interval from the instant of time t5 to the instant of time t6. Furthermore, because the signal (h) becomes the H logic only when both the signal (g) and the signal (b) are the H logic, the signal (h) becomes the H logic only within the interval from the instant of time t5 to the instant of time t6. The D-type flip-flop 50 of the very last stage changes the output signal (i) to the L logic at the instant the signal (h) becomes the up edge.

Accordingly, the oscillator 26 to which the signal (i) is connected is disabled or the interruption switch 29 becomes open (non-conductive state), and the supply of drive energy that has been conducted to the ultrasound vibrator 6 is terminated.

Therefore, the present embodiment has the following effects.

Because a fluid is supplied between the ultrasound probe 9 and the outer cover tube 10, the foreign matter such as body fluid or tissue is prevented from penetrating between the distal end portion 9a of the probe 9 and the outer cover tube 10. Therefore, the drive impedance of the ultrasound puncture treatment tool 2 during puncturing can be reliably detected and the puncture state can be detected with good accuracy.

Furthermore, the circuits for detecting, deciding, and terminating the puncture with the ultrasound puncture treatment tool 2 are simplified and can be fabricated at a low cost.

Second Embodiment

Figure 6:
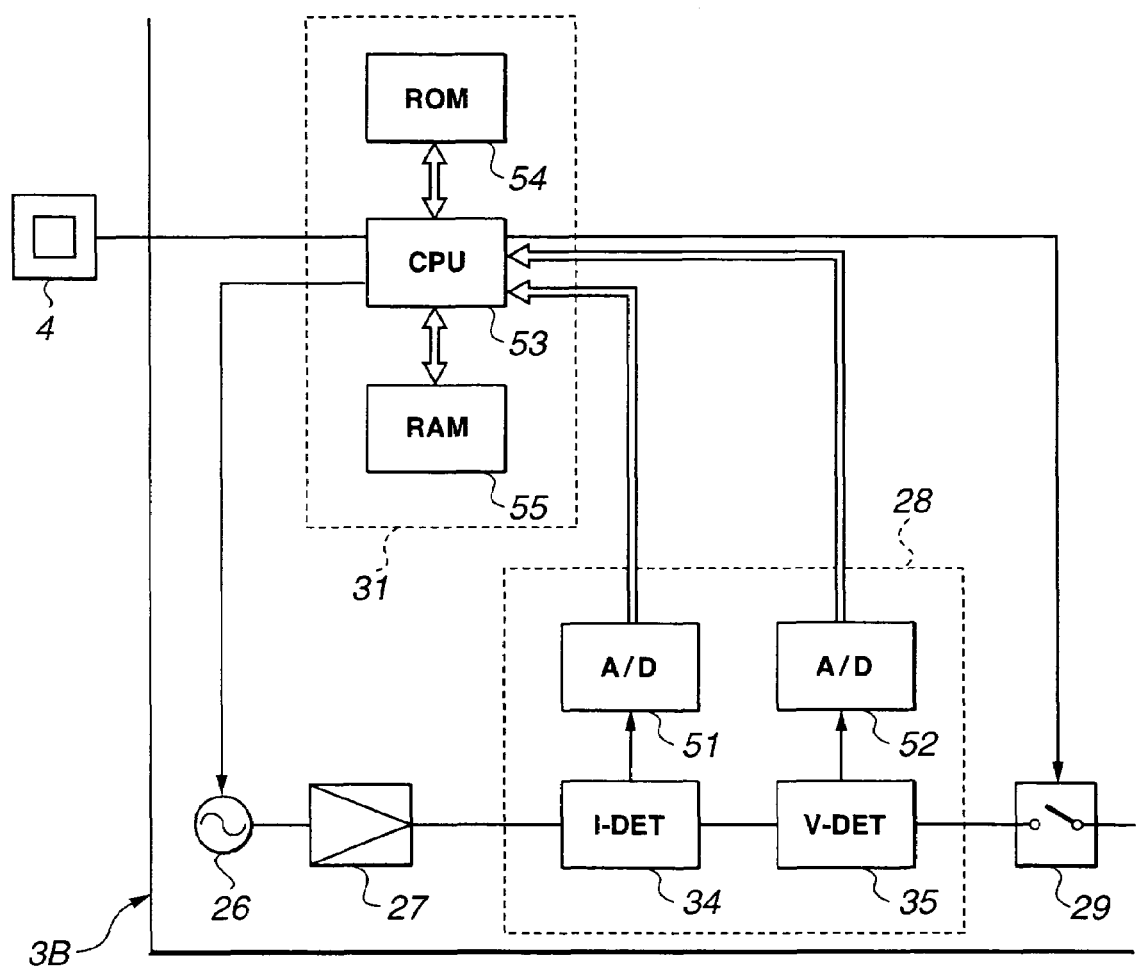
FIG. 6 is a block diagram illustrating the main components of the power source unit in the ultrasound puncture system of a second embodiment of the present invention.

A second embodiment of the present invention will be described hereinbelow with reference to FIG. 6 and FIG. 7. FIG. 6 shows the internal configuration of the main part inside a power source unit 3B in the second embodiment of the present invention. In the power source unit 3B in the present embodiment, the impedance detection circuit 28 is composed of current detection means 34 for detecting the electric current component of the drive signal outputted from the amplifier 27, voltage detection means 35 for detecting the voltage component, and A/D converters 51, 52 for converting the respective analog signals of the detection circuits 34, 35 to digital data.

Furthermore, control means 31 is composed of a CPU 53 for inputting digital data on the electric current and voltage from the A/D converters 51 and 52 respectively, a ROM 54 connected to the CPU 53 and storing (memorizing) the operation program of the CPU and the data relating to this operation, and a RAM 55 used as a work area of the CPU 53 or temporarily storing data for processing.

Figure 7:
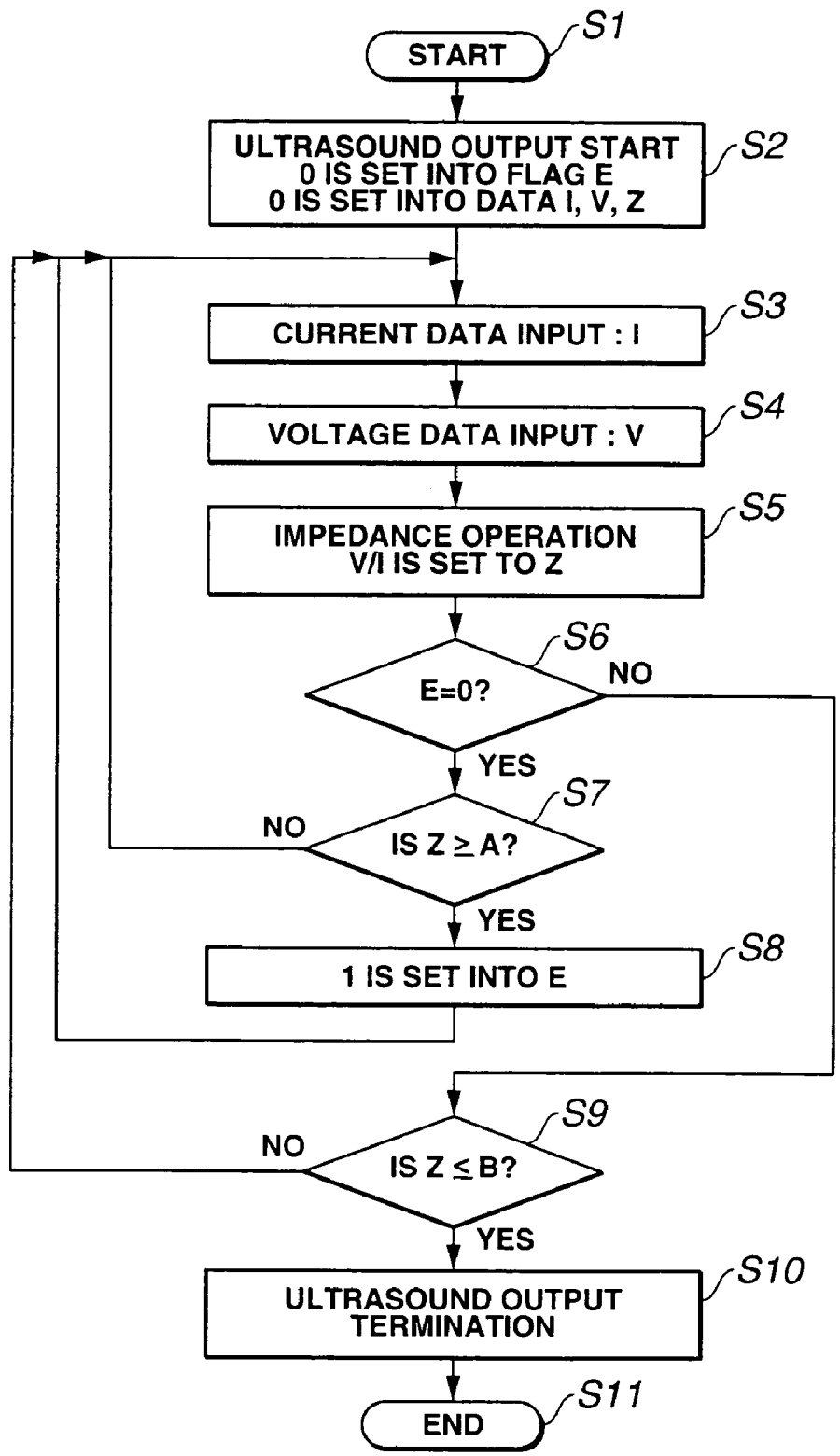
FIG. 7 is a flowchart illustrating the operation of the ultrasound puncture system of the second embodiment.

As shown in detail in FIG. 7, the CPU 53 fetches the digital data that were obtained by detection with the current detection means 34 and voltage detection means 35 and conversion with the A/D converters 51 and 52 conducts an operation of computing the impedance, conducts an operation of comparing the impedance with the threshold A explained in the first embodiment, and conducts processing for deciding as to whether or not the puncture has been reliably made.

In other aspects, the configuration of the ultrasound puncture treatment tool 2 is identical to that of the first embodiment and the explanation thereof will be omitted.

A method for detecting the drive impedance in the aforesaid configuration, that is, the processing sequence executed by the CPU 53, will be described below with reference to the flowchart shown in FIG. 7.

The ultrasound puncture treatment tool 2 is connected to the power source unit 3B, and the treatment is started in step S1 by turning ON the power source switch.

In the next step S2, the ultrasound output is started in the output switch 4 serving as the output switch. Furthermore, in this step, 0 is substituted in the flag E and registers I, V, Z, and the initial processing is conducted.

Here, registers I, V, and Z are the storage registers for storing the data for electric current, the data for voltage, and the data for impedance, respectively, for example, in the CPU 53 (storage areas set in the RAM 55 may be also used).

In the next step S3, the CPU 53 saves the electric current data detected via the A/D converter 51 in the register I. In the next step S4, the detected voltage data are saved in the register V. The CPU 53, in the next step S5, performs the operation of computing the impedance, that is, V/I, by using the current data saved in the register I and voltage data saved in the register V, and saves the results in the register Z.

Then, in step S6, the CPU 53 decides as to whether or not the flag E is 0, and a transition to step S3 or step S9 is made according to the decision result.

In other words, if the decision in step S6 is YES, a decision is made in the next step S7 as to whether or not a drive impedance Z is larger than the threshold A. A transition to step S8 or step S3 is made according to the decision results.

If the decision in step S7 is YES, then 1 is substituted to flag E in step S8.

If the decision in step S7 is NO, the processing flow returns to step S3 and the processing from step S3 to step S7 are repeated. As a result of this processing repetition, the drive impedance detected in the operation increases and exceeds the threshold A. If a decision is made in step S7 that the threshold A has been exceeded, the processing flow proceeds to step S8 and returns to step S3 after the flag E has been set to 1.

In this case, the flag E=1 in step S6. Therefore, a transition is made to step S9.

In step S9, the CPU 53 makes a decision as to whether or not the drive impedance Z detected by the operation is less than the threshold B. A transition to step S3 or step S10 is made according to the decision results. In the present step S9 a decision is made that the drive impedance Z increased at the time of puncture and that the drive impedance Z became less than the fixed value when the skin tissue 21 has been penetrated.

In step S9, when the drive impedance Z detected by the operation is larger than the threshold B, the processing flow returns to step S3, the processing of steps S3 to S6 are performed, and the decision of step S9 is made again.

If a decision made based on the results obtained is that the drive impedance Z became equal to or less than the threshold B, the processing flow makes a transition to step S10, and the ultrasound output is terminated in this step S10. In the next step S11, the puncture treatment with ultrasound waves is ended, for example, by turning OFF the power source switch.

Therefore, the present embodiment has the following effects.

In this embodiment, in addition to the effects of the first embodiment, designing can be conducted with a software. Therefore, a design that does not depend on temperature characteristic or spread can be obtained, and the design can be provided with flexibility with respect to a variation of constants or timing of data detection.

Further, it goes without saying that a correlation may be also provided which describes the relationship with the threshold A and threshold B by a certain function according to the amount of the ultrasound energy which is outputted and the shape of the handpiece for puncturing, or a variety of other treatments can be executed by setting two or more thresholds.

Figure 8:
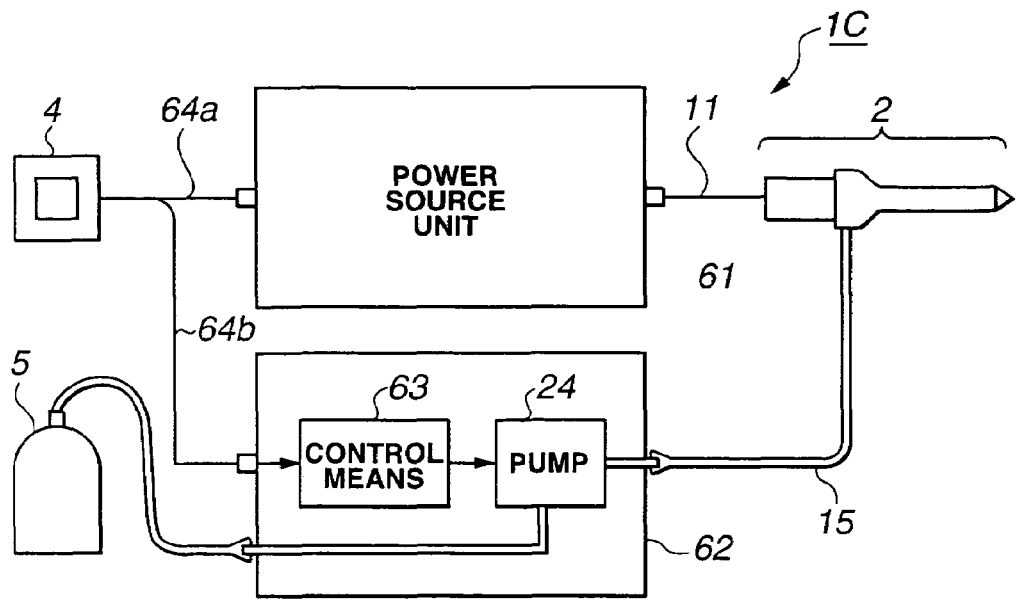
FIG. 8 illustrates a configuration of the first modification example of the ultrasound puncture system of the second embodiment.

A first modification example of the present embodiment will be explained hereinbelow with reference to FIG. 8. FIG. 8 shows an ultrasound puncture system 1C of the first modification example. The ultrasound puncture system 1C has a configuration of the ultrasound puncture system 1 shown in FIG. 2 in which the pump 24 that was contained inside the power source unit 3 (strictly speaking, the power source unit 3B shown in FIG. 6) is used as a separate unit and a power source unit 61 and a pump unit 62 are separated.

In other words, the power source unit 61 has a configuration in which the pump 24 is removed from the power source unit 3, as shown in FIG. 2.

Further, the pump unit 62 is provided, as a unit separate from the power source unit 61, for supplying and interrupting the supply of a fluid. The pump unit 62 has a configuration composed of control means 63 providing for the control of the entire pump unit 62 and the pump 24 for supplying and interrupting the supply of a fluid.

The output switch 4 is connected to the power source unit 61 and pump unit 62 (control means 31, 63 thereof) via a pair of cables 64a, 64b and the connectors at the end portions thereof, so that SW signals can be transmitted.

When the output switch is pushed down and switched ON, the power source unit 61 supplies ultrasound energy and the pump unit 62 supplies a fluid to the ultrasound puncture treatment tool 2. All other structure are identical to those of the second embodiment.

The operation effect of the present modification example is almost identical to that of the second embodiment.

As an additional effect of the present modification example can be realized only by additionally providing an output switch 4 with the already present power source unit 61 and pump unit 62 (with the configuration shown in FIG. 8). In other words, the flexibility of application is improved.

Figure 9:
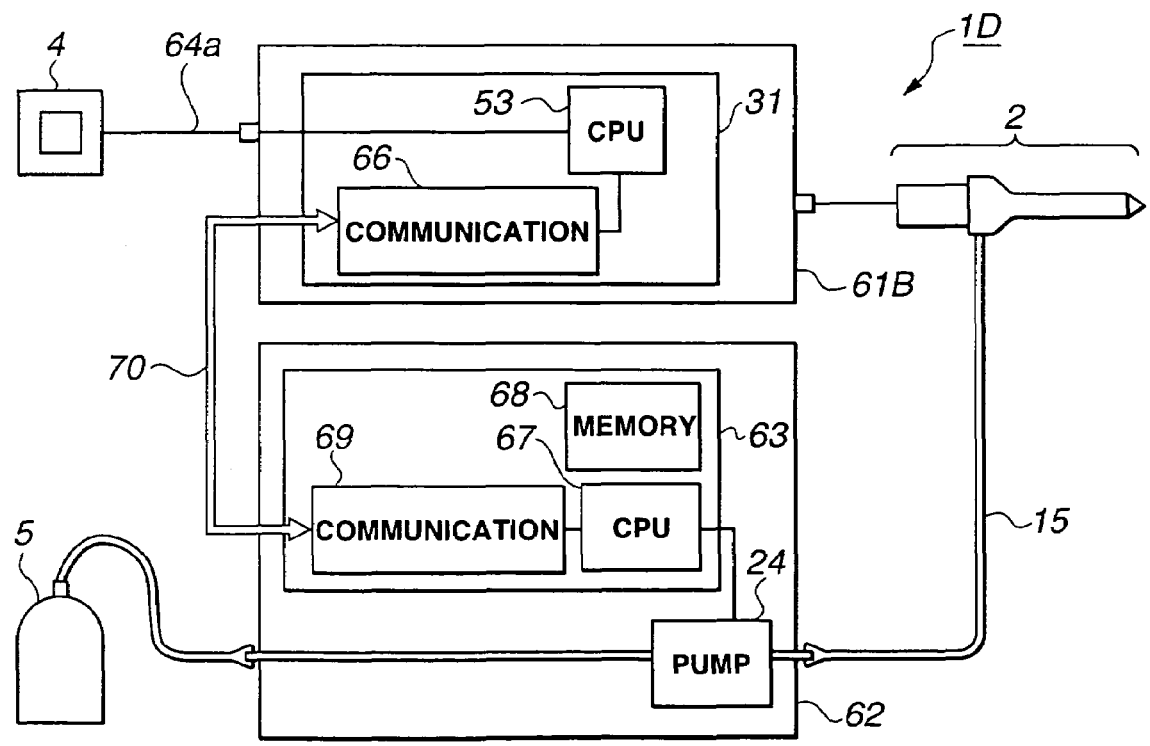
FIG. 9 illustrates a configuration of the second modification example of the ultrasound puncture system of the second embodiment.

FIG. 9 shows an ultrasound puncture system ID which is the second modification example obtained by modifying the first modification example. This ultrasound puncture system 1D has separate power source unit 61B and pump unit 62B, as shown in FIG. 8. In the configuration shown in FIG. 8, the two cables 64a, 64b extending from the output switch 4 were connected to the power source unit 61 and pump unit 62, but in the present embodiment, the output switch 4 has a configuration such that only one cable 64a may be connected to the control means of the power source unit 61B.

For this purpose, in the present embodiment, control means 31 is provided with communication means 66. FIG. 9 shows only CPU 53 and communication means 66 as the control means 31, but it also comprises the ROM 54 and RAM 55 as shown in FIG. 6.

Further, the pump unit 62B comprises a memory 68 in addition to the CPU 67 for controlling the pump 24, as control means 63, and communication means 69 for conducting communication with the aforesaid communication means 66. The communication means 66, 69 are connected and conduct communication with a communication cable 70.

In this system 1D, the operation is realized by the transmission and reception via communication means 66 and communication means 69 of the signal instructing the pump unit 62B to start the fluid supply synchronously, before, or after the timing at which the power source unit 61B supplies the electric energy for outputting ultrasound waves to the ultrasound puncture treatment tool 2.

In the present system 1D, the output switch 4 is connected to the power source unit 61B, but the same functions can be realized by connecting it to the pump unit 62B.

As for the communication path, in addition to the wire-based signal transmission means using the cable 70, other signal transmission means may be employed, examples of such means including optical signal transmission means using light emitting and receiving elements and wireless signal transmission means using emission and reception of electromagnetic waves.

The second modification example has the following effects.

The effect almost identical to that of the system 1C shown in FIG. 8 is obtained. In addition, with the present modification example, connecting the output switch 4 to only one of the power source unit 61 and pump unit 62, rather than to both units, makes it possible to realize the same functions, and a system which is easier to use can be realized.

Third Embodiment

Figure 10:
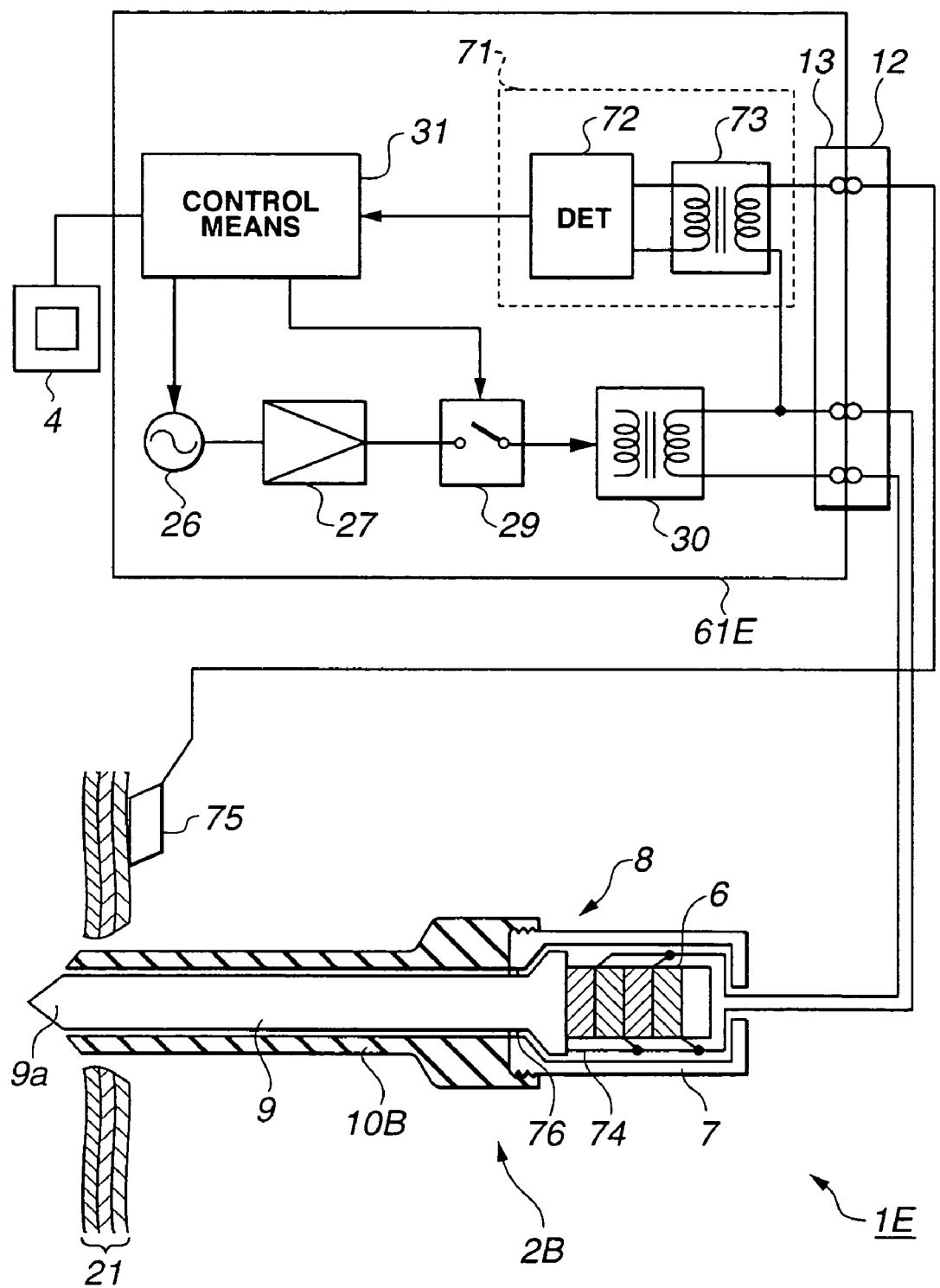
FIG. 10 illustrates the overall configuration of the ultrasound puncture system of a third embodiment of the present invention.

A third embodiment of the present invention will be described hereinbelow with reference to FIG. 10. FIG. 10 shows an ultrasound puncture system 1E of the third embodiment of the present invention.

The ultrasound puncture system 1E employs a power source unit 61E that does not contain the pump 24, as shown, for example, in FIG. 8. Thus, in the present embodiment, for example, a ultrasound puncture treatment tool 2B is obtained which employs an outer cover tube 10B formed from an electrically insulating, that is, non-conductive member, without providing a socket 14 (for connecting the tube 15) shown, for example, in FIG. 2.

Further, the present embodiment employs impedance detection means 71 which is different from those of the first and second embodiments.

In the above-described embodiments, impedance detection means 28 was provided between the amplifier 27 and interruption switch 29, but in the present embodiment, it is provided in a different location, as shown in FIG. 10.

Further, impedance detection means 71 in the present embodiment comprises detection and decision means 72 and insulating means 73.

One terminal of an insulating transformer forming the insulating means 73 is connected to one terminal of the insulating transformer 30, connected to one electrode of the ultrasound vibrator 6 of the ultrasound puncture treatment tool 2B. Moreover, this one electrode is electrically connected to the probe 9 with a connection line 74. Furthermore, the other terminal of the insulating transformer forming the insulating means 73 is connected to an electrode 75 applied (pasted) to the skin tissue 21 in the vicinity of the zone where the treatment by puncturing with the distal end of probe 9 is conducted.

In the above-described embodiments, because the fluid is supplied to the outer cover tube 10 with the pump 24 and released at the distal end portion 9a of the probe, the supply is conducted so that body fluids or tissue do not penetrate between the probe 9 and outer cover tube 10. It is preferred that a non-conductive liquid and gas to be used as the supplied liquid, this being a limitation. By contrast, in the present embodiment, fluid supply is not used due to the above-described configuration, and impedance detection means 71 is formed such that allows the end of puncture treatment to be detected with good accuracy.

Further, the inner side of the front end of the vibrator accommodating unit 7 is sealed, for example, with an O ring 76 so as to prevent the penetration of body fluids and the like.

All other structural aspects are identical to those of the above-described embodiments, the identical structural components are assigned with the same reference symbols, and the explanation thereof is omitted.

A specific feature of the present embodiment is that impedance detection means 71 is formed which does not use the fluid supply, as described hereinabove.

More specifically, in the present embodiment, the impedance detection means 71 detects the impedance between the probe 9 and electrode 75. In this case, the skin tissue 21 which is in contact with the distal end portion 9a is present between the probe 9 and electrode 75 because the puncture treatment is conducted by the distal end portion 9a of the probe 9, and an extremely high impedance is obtained when the skin tissue 24 is pierced by the distal end portion 9a of the probe 9 and the contact (with the skin tissue 24 at the instant the puncture has been conducted) is lost.

The impedance changes are detected by the detection and decision means 72 and an action is executed which transmits a signal for interrupting ultrasound energy supply to control means 31.

Figure 11:
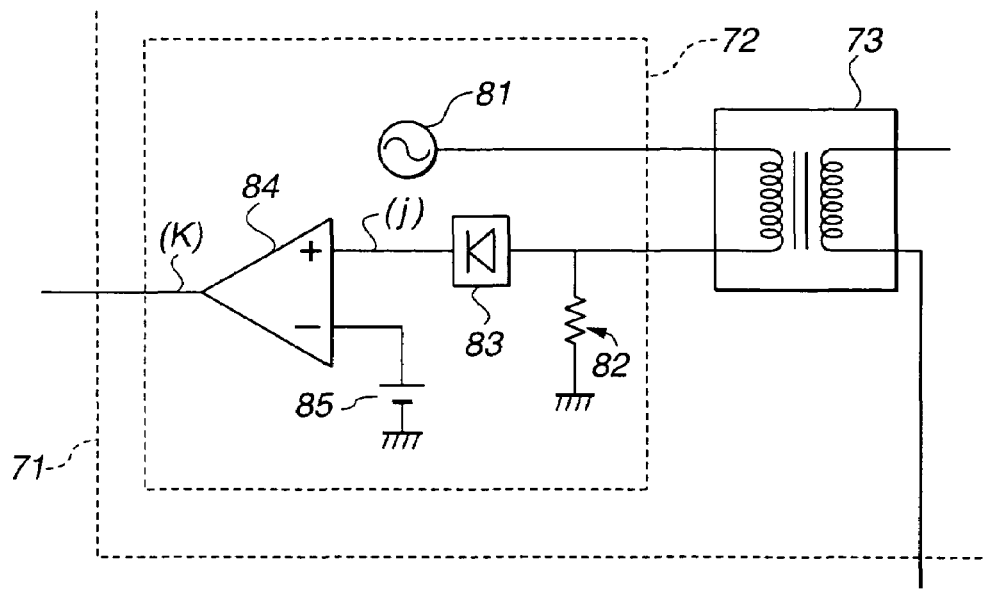
FIG. 11 is a circuit diagram illustrating the internal configuration of the detection and decision means in the ultrasound puncture system of the third embodiment.

FIG. 11 illustrates an example of the internal configuration of the detection and decision means 72.

The detection and decision means 72 is composed of an oscillator 81, a resistor 82, a rectifying and smoothing means 83, a comparator 84, and a reference voltage 85.

The AC waveform generated in the oscillator 81 is converted in insulating means 73 via the impedance between the probe 9 and electrode 75 and divided with the resistor 82. The divided AC signal is transmitted to the rectifying and smoothing means 83 to obtain a rectified and smoothed signal (j), which is applied to one input terminal of comparator 84. The signal (j) is then compared with the voltage value of the reference voltage 85 that has been applied to another input terminal of the comparator 84, and a signal (k) representing a comparison result is outputted from the comparator 84.

Figure 12:
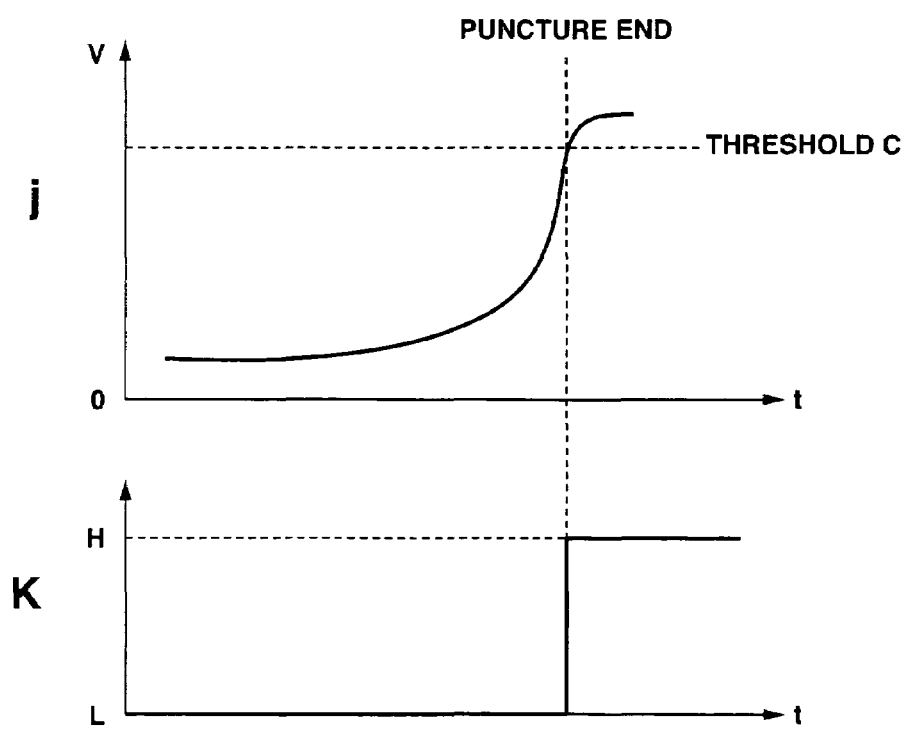
FIG. 12 is a timing chart illustrating the operation of the detection and decision means in the ultrasound puncture system of the third embodiment.

FIG. 12 shows the operation waveforms of the input signal (j) supplied from the rectifying and smoothing circuit 83 to the comparator 84 and the output signal (k) of the comparator 84.

The impedance between the probe 9 and electrode 75 changes as shown by the solid line (j) and rapidly changes to an extremely high value at the instant of time the puncturing has ended. Based on the results of comparison of this impedance with the threshold C appearing in the reference voltage 85, the logic of the output signal (k) changes from the L logic to the H logic, and if the signal with the H logic is received, the control means 31 stops the oscillation by the oscillator 26, the interruption switch 29 is opened, and the ultrasound output is terminated.

Furthermore, it goes without saying that the replacement of the comparator 84 with an A/D converter for analog-digital conversion of the reference voltage 85 makes it possible to modify variously the processing of detected digital data, not only in the convenient, in terms of impedance, case in which the signal reception means of control means 31 is programmable digital means such as CPU.

Accordingly, the present modification has the following effects.

In addition to the effects of the above-described modifications, because fluctuations of the force pressing the probe 9 against the skin tissue 21 produce no effect on the impedance detection results, the puncturing end can be accurately detected, without affecting the operation method.

Figure 13:
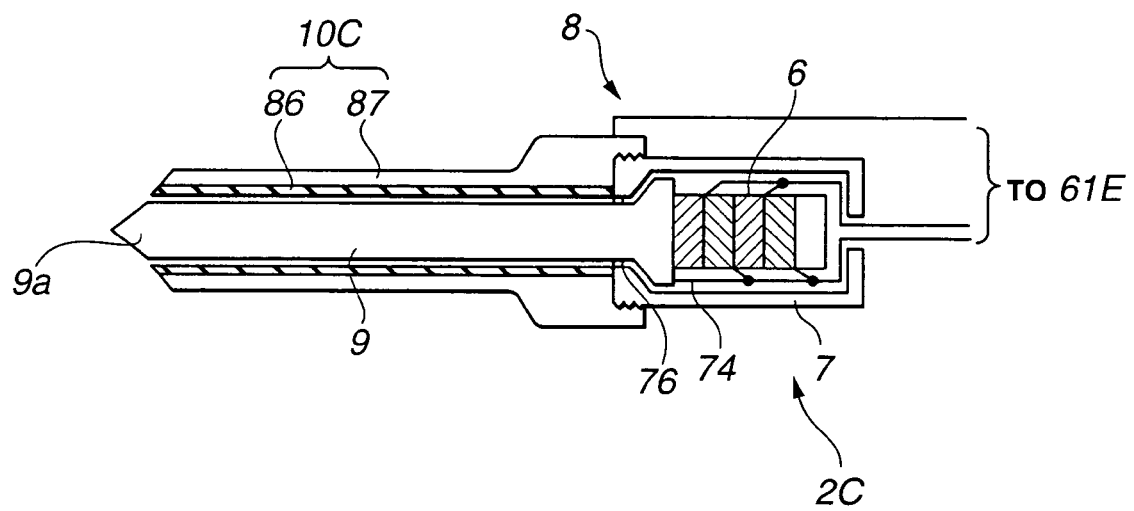
FIG. 13 shows the configuration which is a first modification example of the ultrasound puncture system of the third embodiment.

FIG. 13 shows an ultrasound puncture treatment tool 2C of the first modification example. This ultrasound puncture treatment tool 2C is provided with the functions of the electrode 75 and the ultrasound puncture treatment tool 2B shown in FIG. 10.

In this ultrasound puncture treatment tool 2C, an outer cover tube 10C which is formed from an electrically conductive member provided inside thereof with an cylindrical inner tube 86 formed from a non-conductive member and which has the function of electrode 87 is employed instead of the outer cover tube 10B formed from a non-conductive member that was used in the ultrasound puncture treatment tool 2B shown in FIG. 10. In other words, the probe 9 is electrically insulated with the inner tube 86 formed from an electrically conductive member disposed on the outer periphery thereof, and even if the biological tissue enters into the outer peripheral surface of the probe 9, no adverse effect is produced on the impedance detection and the puncture end, that is, the penetration state, can be detected with good accuracy.

The electrode 87 is connected to the insulating means 73 of a power source unit 61E via a cable.

As a result, the decision is made that the puncture has ended when no skin tissue 21 is present anymore between the electrode 87 and probe 9, and such a decision can be made with good accuracy.

The present modification example has the following effects.

In addition to the effects of the above-described embodiments, because the electrode 87 is integrated with the outer cover tube 10, the wiring is streamlined and the difficulty of applying the electrode to a special patient is eliminated.

Furthermore, because the actual distance between the electrode 87 and probe 9 is decreased, the electric power that has to be supplied from the impedance detection means during impedance detection can be reduced.

Figure 14:
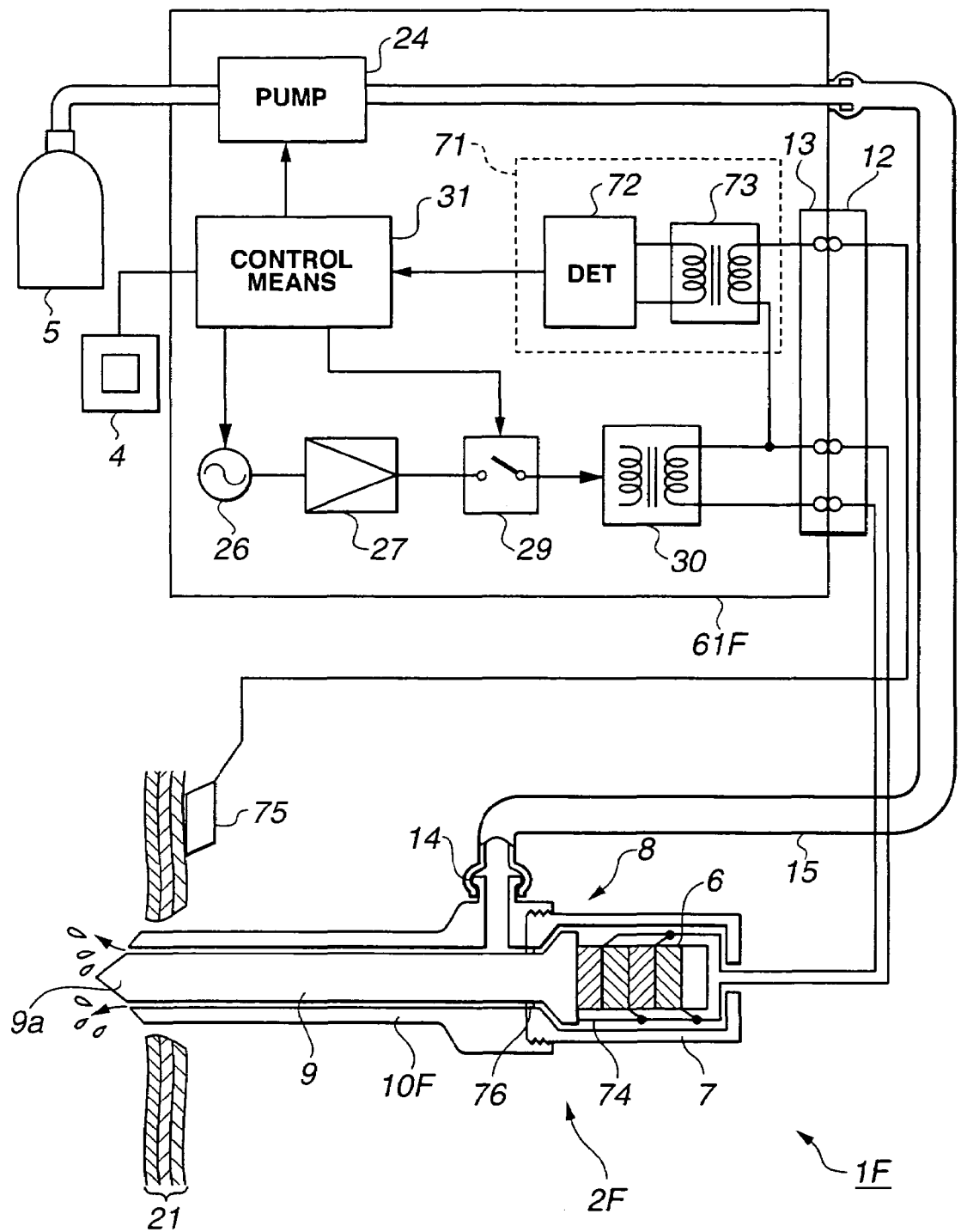
FIG. 14 shows the overall configuration of the ultrasound puncture system which is a second modification example of the ultrasound puncture system of the third embodiment.

FIG. 14 shows an ultrasound puncture system 1F which is the second modification of the third embodiment. The present system 1F employs a power source unit 61F containing the pump 24 for supplying a fluid and an ultrasound puncture treatment tool 2F using an outer cover tube 10F provided with a socket 14 corresponding to the power source unit 61F.

The power source unit 61F has the configuration of the power source unit 61E shown in FIG. 10, which comprises the pump 24 inside thereof. The fluid is supplied to the ultrasound puncture treatment tool 2F via the tube 15.

In other words, the present system 1F has a configuration such that in the system 1E shown in FIG. 10, the fluid is supplied to the outer cover tube 10F with the pump 24 and released at the distal end portion 9a of the probe 9, thereby preventing the body fluids and tissue from entering between the probe 9 and the outer cover tube 10F. In this case, the supplied fluid is preferably a non-conductive liquid or gas.

As for the impedance detection, the impedance between the probe 9 and electrode 75 is detected, similarly to the system 1E shown in FIG. 10, and a very high impedance is detected when the distal end portion 9a of the probe 9 pierces the skin tissue 21 and looses contact therewith.

Changes in the impedance are detected with detection and decision means 72 and a signal is transmitted for interrupting the supply of electric energy of ultrasound output to control means 31.

Here, it is important that no electric connection should be provided by the body fluids or tissue between the probe 9 and skin tissue 21 in order to obtain an impedance during the puncture end which is sufficiently high by comparison with a low impedance resulting from the contact of the probe 9 and skin tissue 21 during puncturing.

Accordingly, it is necessary to supply fluid with the pump 24 and conduct flushing.

The present embodiment has the following effects.

In addition to the effects of the above-described embodiments, the puncture end can be detected with even higher accuracy because the probe 9 and skin tissue 21 are prevented from being electrically connected by body fluids or tissue, with the object of obtaining an impedance during puncture end which is sufficiently high by comparison with a low impedance resulting from the contact of the probe 9 and skin tissue 21 during puncturing.

Figure 15:
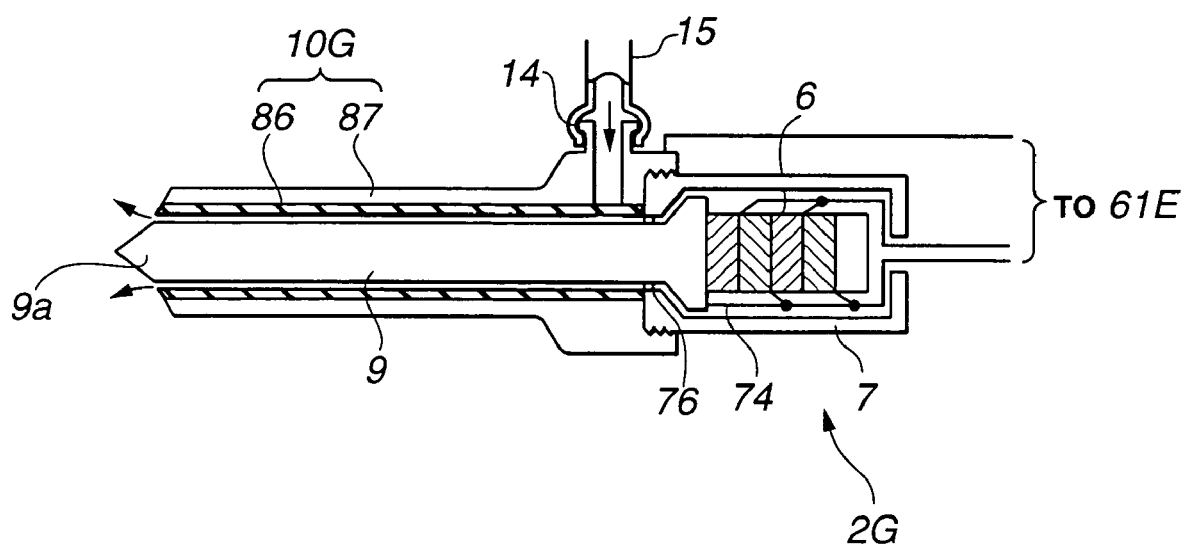
FIG. 15 shows the configuration of the treatment tool for ultrasound puncture used in the ultrasound puncture system which is the second modification example of the ultrasound puncture system of the third embodiment.

FIG. 15 shows an ultrasound puncture treatment tool 2G which is a modification example of the ultrasound puncture treatment tool 2F used in the ultrasound puncture system 1F shown in FIG. 14.

The ultrasound puncture treatment tool 2G has a configuration corresponding to that of the ultrasound puncture treatment tool 2C shown in FIG. 13, which is provided with the socket 14.

More specifically, an outer cover tube 10G which is formed from an electrically conductive member provided inside thereof with a cylindrical inner tube 86 formed from a non-conductive member and which has the function of electrode 87 is employed instead of the outer cover tube 10F that was used in the ultrasound puncture treatment tool 2F shown in FIG. 14.

Further, the electrode 87 is connected to insulating means 73 of the power source unit 61F via a cable.

With such a configuration, the decision is made that the puncture has ended when no skin tissue 21 is present anymore between the electrode 87 and probe 9.

The present modification example has the effects identical to those of the example illustrated by FIG. 13.

Figure 16:
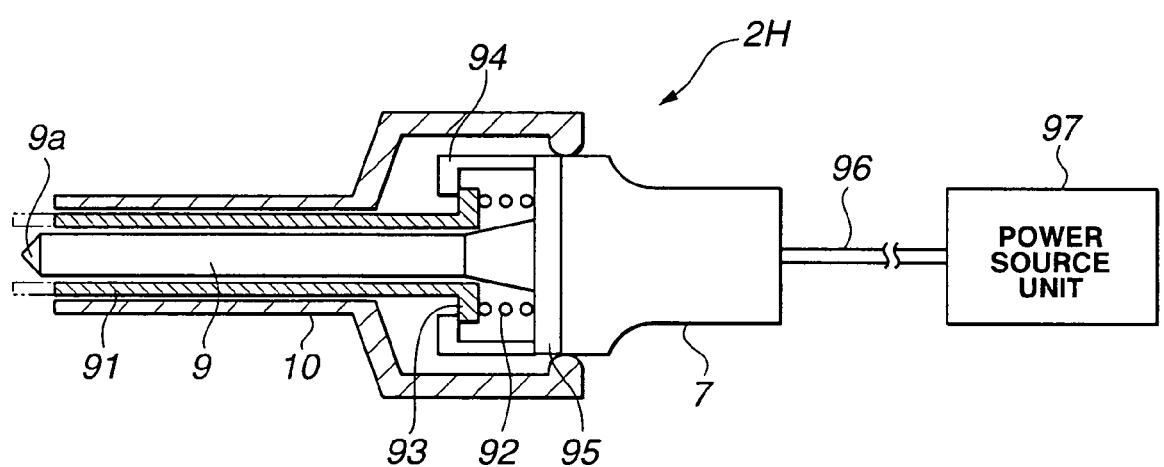
FIG. 16 shows schematically the configuration of the treatment tool for ultrasound puncture provided with a lock mechanism

Further, it is also possible, as in an ultrasound puncture treatment tool 2H shown in FIG. 16, to provide a cylindrical sheath (functioning as a protective member) 91 between the probe 9 and the outer cover tube 10, to impel the base end of the sheath 91 so that it protrudes forward (distal end side) by a coil spring 92, and to form a lock mechanism by providing a drive portion 95 at the base end so that, for example, the flange portion 93 at the base end of the sheath 91 is normally engaged with the hook portion of a lock member 94, and is locked preventing the sheath from protruding.

This ultrasound puncture treatment tool 2H is connected with a cable 96 to the power source unit 97.

When the penetration of the distal end portion 9a with a pointed distal end through the skin tissue 21 such as stomach wall is detected by the changes in the impedance in the impedance detection circuit of the power source unit 97, as in the aforesaid embodiments, a signal (of lock release) is sent to the drive unit 95, and the drive unit 95 moves the lock member 94 constituting the lock mechanism toward the outside with a motor, or rotates it and moves forward, thereby releasing the locked state of engagement with the flange portion 93 of the sheath 91.

As a result of this release of the lock mechanism, the distal end of the sheath 91 may protrude forward from the distal end portion 9a of the probe 9, as shown by a two-dot line, under the effect of the impelling force of the coil spring 92, thereby preventing the distal end portion 9a of the probe from coming into contact with the internal organs or the like.

Furthermore, with the lock mechanism shown in FIG. 16, when the lock mechanism was released, the sheath 91 was caused to protrude forward (so that the distal end thereof moved forward beyond the pointed distal end of the probe 9) under the effect of the impelling force of the coil spring 92, but this configuration is not limited to. For example, a configuration may be also used in which an electric current flows into an electromagnet and a plunge is driven by the output of the impedance detection circuit when the skin tissue 21 is penetrated, and the sheath 91 is caused to move forward by this plunger.

The present invention also covers the embodiments configured by partial combinations of the aforesaid embodiments.

In this invention, it is apparent that working modes different in a wide range can be formed on this basis of this invention without departing from the spirit and scope of the invention. This invention is not restricted by any specific embodiment except being limited by the appended claims.

What is claimed is:

1. A ultrasound puncture system comprising:
   a handpiece which accommodates an ultrasound vibrator as ultrasound wave generating means;
   a puncturing probe having a pointed distal end portion that punctures a biological wall and penetrates through said biological wall by transmitting ultrasound waves to said biological wall which is to be punctured;
   an outer cover tube which covers the probe and is detachably attached to the handpiece, said outer cover tube having a distal end portion that punctures said biological wall as the handpiece punctures said biological wall, and penetrates through said biological wall as the handpiece penetrates trough said biological wall;
   an ultrasound power source unit for supplying energy for driving the ultrasound vibrator;
   termination means installed in the ultrasound power source unit for terminating the energy supply to the ultrasound vibrator;
   impedance detection means installed in the ultrasound power source unit for detecting the puncture state when the probe punctures the biological wall;
   electric current detection means for detecting the electric current component of the energy supplied to the ultrasound vibrator;
   voltage detection means for detecting the voltage component of the energy;
   operation means for deriving the impedance from the detection results of the electric current and voltage detection means; and
   decision means for deciding that the probe has penetrated the biological wall based on the results of the operation means.

2. The ultrasound puncture system according to claim 1, wherein
   there is a space open from the base end portion of the probe to the distal end portion of the probe between the outer cover tube and the probe;
   the ultrasound power source unit comprises fluid supply means for supplying a fluid to the space; and the penetration of the probe through the biological wall is detected with the impedance detection means and the supply of energy to the ultrasound vibrator is terminated by the detection output.

3. The ultrasound puncture system according to claim 1, wherein the penetration through said biological wall is judged based upon whether the impedance is below a predetermined threshold value.

4. The ultrasound puncture system according to claim 3, wherein
each of the electric current detection means and the voltage detection means is provided with an A/D converter for converting the detection results into digital data.

5. The ultrasound puncture system according to claim 1, wherein
a first electrode and a second electrode are provided in the ultrasound power source unit;
one of the electrodes is connected to so as provide for electric conductivity to the probe; and
the system further comprises discrimination means for converting the impedance between the electrodes and judging the results detected with the impedance detection means.

6. A ultrasound puncture system comprising:
a handpiece which accommodates an ultrasound vibrator as ultrasound wave generating means;
a puncturing probe for transmitting ultrasound waves to a biological wall which is to be punctured;
an outer cover tube which covers the probe and is detachably attached to the handpiece;
an ultrasound power source unit for supplying energy for driving the ultrasound vibrator;
termination means installed in the ultrasound power source unit for terminating the energy supply to the ultrasound vibrator; and
impedance detection means installed in the ultrasound power source unit for detecting the puncture state when the probe punctures the biological wall, wherein
the penetration of the probe through the biological wall is detected with the impedance detection means and the supply of energy to the ultrasound vibrator is terminated by the detection output wherein a first electrode and a second electrode are provided in the ultrasound power source unit;
one of the electrodes is connected to so as provide for electric conductivity to the probe; and
the system further comprises discrimination means for converting the impedance between the electrodes and judging the results detected with the impedance detection means; wherein
the outer cover tube is composed of a non-conductive member and a conductive member;
the non-conductive member is disposed on the inner surface of the outer cover tube, which is in contact with the probe; and
the second electrode is electrically connected to the conductive member of the outer cover tube.

7. A ultrasound puncture system comprising:
a handpiece which accommodates an ultrasound vibrator as ultrasound wave generating means;
a puncturing probe for transmitting ultrasound waves to a biological wall which is to be punctured;
an outer cover tube which covers the probe and is detachably attached to the handpiece;
an ultrasound power source unit for supplying energy for driving the ultrasound vibrator;
termination means installed in the ultrasound power source unit for terminating the energy supply to the ultrasound vibrator; and
impedance detection means installed in the ultrasound power source unit for detecting the puncture state when the probe punctures the biological wall, wherein
the penetration of the probe through the biological wall is detected with the impedance detection means and the supply of energy to the ultrasound vibrator is terminated by the detection output; wherein
means for supplying the energy to the ultrasound vibrator and fluid supply means for supplying a fluid into the space between the outer cover tube and the probe are separate units;
each of those units comprises communication means for causing them to operate in response to each other; and
fluid supply means supplies the fluid to the vibrator via the communication means in response to the energy supply.

8. A ultrasound puncture system comprising:
a handpiece which accommodates an ultrasound vibrator as ultrasound wave generating means;
a puncturing probe for transmitting ultrasound waves to a biological wall which is to be punctured;
an outer cover tube which covers the probe and is detachably attached to the handpiece;
an ultrasound power source unit for supplying energy for driving the ultrasound vibrator;
termination means installed in the ultrasound power source unit for terminating the energy supply to the ultrasound vibrator; and
impedance detection means installed in the ultrasound power source unit for detecting the puncture state when the probe punctures the biological wall, wherein
the penetration of the probe through the biological wall is detected with the impedance detection means and the supply of energy to the ultrasound vibrator is terminated by the detection output; wherein a sheath is further disposed between the probe and the outer cover tube, and means is provided for causing the distal end of the sheath to protrude forward beyond the distal end portion of the probe in response to an output of the impedance detection means that detected that the distal end portion of the probe has penetrated through the biological wall.

* * * * *